(12) United States Patent
Saranin et al.

(10) Patent No.: US 11,607,328 B2
(45) Date of Patent: Mar. 21, 2023

(54) DEVICE AND METHOD FOR SAFELY POSITIONING A CORONARY STENT IN THE CORONARY ARTERIES

(71) Applicant: SEVEN SONS LTD. R.N. 515985570 (THE "COMPANY"), Tel Aviv (IL)

(72) Inventors: Sergei Alexandrovich Saranin, Serpukhov (RU); Anton Alexandrovich Kobak, St.Petersburg (RU)

(73) Assignee: SEVEN SONS LTD., Tel Aviv (IL)

( * ) Notice: Subject to any disclaimer, the term of this patent is extended or adjusted under 35 U.S.C. 154(b) by 939 days.

(21) Appl. No.: 16/473,400

(22) PCT Filed: Apr. 14, 2017

(86) PCT No.: PCT/RU2017/000234
§ 371 (c)(1),
(2) Date: Jun. 25, 2019

(87) PCT Pub. No.: WO2018/124923
PCT Pub. Date: Jul. 5, 2018

(65) Prior Publication Data
US 2019/0328560 A1    Oct. 31, 2019

(30) Foreign Application Priority Data

Dec. 30, 2016   (RU) ............................ RU2016152735

(51) Int. Cl.
*A61F 2/962* (2013.01)
*A61F 2/95* (2013.01)
*A61B 17/00* (2006.01)

(52) U.S. Cl.
CPC ............... *A61F 2/962* (2013.01); *A61F 2/95* (2013.01); *A61B 2017/00243* (2013.01); *A61F 2/9517* (2020.05); *A61F 2/9522* (2020.05)

(58) Field of Classification Search
CPC .......... A61F 2/95; A61F 2/9517; A61F 2/954; A61F 2/962; A61F 2/966; A61B 17/2909;
(Continued)

(56) References Cited

U.S. PATENT DOCUMENTS

| 6,293,964 B1 | 9/2001 | Yadav |
| 2013/0253423 A1* | 9/2013 | Shin ................... A61M 25/0113 604/95.01 |

FOREIGN PATENT DOCUMENTS

| EP | 2 363 099 A1 | 9/2011 |
| RU | 2 598 798 | 9/2016 |

(Continued)

OTHER PUBLICATIONS

International Search in International Application No. PCT/RU2017/000234.

(Continued)

*Primary Examiner* — Diane D Yabut
(74) *Attorney, Agent, or Firm* — Ladas & Parry LLP (57) ABSTRACT

The device is a body with a truncated anterior portion and a cylindrical posterior portion, which are interconnected such that the cylindrical posterior portion of the body is rotatable about its own axis. The inside surface of the cylindrical posterior portion of the body is provided with a thread that is capable of engaging a lip of a slider disposed on guides inside the posterior portion of the body. The slider is connected to a barrel of a gripper having vanes with elastic elements at a delivery system gripping point such that the gripper is rotatable about its own axis, wherein the vanes of the gripper have protuberances disposed in a clamping cylinder which is arranged inside the body of the device and squeezes and releases the vanes of the gripper under the action of a release member.

6 Claims, 6 Drawing Sheets

(58) Field of Classification Search
CPC ..... A61B 2017/00243; A61M 25/0113; A61M 25/0136; A61M 2025/09116
See application file for complete search history.

(56) References Cited

FOREIGN PATENT DOCUMENTS

WO     2015/179140 A1    11/2015
WO     2017/052414 A1    3/2017

OTHER PUBLICATIONS

Written Opinion of the International Search Authority in International Application No. PCT/RU2017/000234.
RU 2 598 798 C1—Espacenet English Abstract.

* cited by examiner

DEVICE AND METHOD FOR SAFELY POSITIONING A CORONARY STENT IN THE CORONARY ARTERIES

RELATED APPLICATION

This application is an application under 35 U.S.C. 371 of International Application No. PCT/RU2017/000234 filed on 14 Apr. 2017, which claims priority from Russian Application No. 2016152735 filed 30 Dec. 2016, the disclosures of which are incorporated in their entirety by reference herein.

The present invention is suitable for use in medicine to enable a maximally accurate, fast and safe positioning of a coronary stent in case of uncomplicated and complicated anatomic lesions of the coronary bed, in particular within the coronary artery in case of endovascular surgery by means of coronary stenting for recanalization of the artery portions constricted as a result of lesion.

The inventive device is intended for use in case of coronary ostial lesions, coronary bifurcation lesions including lesions of the left coronary artery trunk and ostial lesions of the right coronary artery as well as in case of "stent in stent" implantation for reducing the "overlap" zone.

The use of this device allows the radiation exposure of patients and medical personnel as well as the exposure of patients to radio-opaque contrast agents to be significantly reduced.

The device may be easily used by young professionals at a time of their professional development in the field of interventional cardiology.

In addition, the claimed device may be also used for stenting renal, visceral arteries in a similar way.

A number of devices for positioning a stent within the coronary artery are available at the medical equipment market.

In particular, U.S. Pat. No. 6,293,964 discloses OSTIAL PRO available from Merit Medica (USA). The device according to this patent comprises a cone made up of four tongues insertable into a guiding catheter together with a coronary stent. The guiding catheter is selectively positioned within the coronary ostium. The coronary stent is guided along the catheter to a location more distal that the coronary ostium whereafter the guiding catheter is withdrawn from the coronary ostium and the device is deployed. As the device leaves the guiding catheter, its tongues unfold and abut against the aortal wall so that the guiding catheter tip cannot be selectively positioned within the coronary ostium as required for ostial stenting of the left coronary artery trunk and the right coronary artery trunk. The entire subsequent positioning of the coronary stent within the affected area is performed manually.

A disadvantage of the known device is its limited applicability, in particular only in cases of ostial lesions of the left coronary artery trunk and the right coronary artery trunk, as well as the manual positioning of the coronary stent.

Also known is a device for a safe positioning of a coronary stent within coronary arteries according to RU Patent No. 2598798 owned by Seven Sons OJSC.

The claimed device differs primarily in:
  faster and more accurate positioning of a coronary stent within coronary artery,
  mechanical positioning rather than manual positioning of the stent,
  reduced radiation exposure of patients and medical personnel due to reduced time of the coronary stent positioning,
  applicability of the device in case of lesions within any segment of the coronary bed,
  reduced exposure of patients to radio-opaque contrast agents due to reduced time of the coronary stent positioning,
  single applicability,
  the device is conveniently configured as extension of the surgeon's arm,
  minimal weight and dimensional parameters,
  ease of use,
  cost-effective production.

The device is industrially applicable.

The claimed device comprises a housing comprising two halves: a truncated front part and a cylindrical rear part. The housing is formed of plastic by injection molding, wherein its surface contacting the operator's arm is pebbled. The housing is provided with a horizontally extending hole for receiving a coronary stent delivery system, the truncated front part of the housing has recesses on its both sides for the operator's left thumb and left forefinger to hold the device fixed in position, wherein the recess for the left thumb also serves as a pad for fixing the coronary guide. The front and rear parts of the housing have holes for insertion of the coronary stent delivery system into the housing.

The cylindrical rear part of the housing is connected to the truncated front part of the housing so as to be rotatable around its axis relative to the said front part.

On an inner surface of the cylindrical rear part of the housing, a thread is circumferentially arranged contacting a protrusion formed on one side of a runner arranged on guides of the front part of the housing and horizontally displaceable along guides inside the housing. On the other side of the runner, a hollow bushing is arranged with a gripping means mounted therein freely rotatably around its axis, said gripping means having flaps with elastic members on one side at the gripping point of the delivery system and arranged inside a pressure roller within the truncated part of the housing comprising two halves and contacting the release mechanism flaps arranged at an angle to each other and to the pressure roller, said release mechanism being provided with a pressure surface on an outer surface of the truncated part of the housing.

A release means is arranged in the truncated front part of the housing, comprising a pressure surface on an outer side of the truncated front part of the housing, and flaps arranged inside the housing at an angle to each other and contacting the pressure roller which, when pressure is exerted by the flaps of the release means, contracts to open the flaps, and, when no pressure is exerted thereon, opens to close the flaps of the gripping means so that the coronary stent delivery system may by rigidly fixed as it moves both forwards and backwards. When pressure is exerted to the pressure surface arranged on an outer side of the housing, the release means flaps press onto the pressure roller which causes the protrusions on the gripping means flaps to contract so that the flaps with elastic members at the gripping point of the delivery system that are arranged inside the bushing freely rotatably around its axis open to set free a through hole in the gripping means for placing the coronary stent delivery system inside the device following which the pressure surface is released, the gripping means flaps, the pressure roller and the protrusions on the gripping means flaps return to their initial position and the flaps with elastic members fix the delivery system, the operator causes the cylindrical rear part of the housing to rotate circumferentially with his/her right arm for advancing the delivery system longitudinally to a necessary distance forwards or backwards along the guides at the operator's discretion due to engagement of the runner protrusion with the internal thread of the cylindrical rear part of the housing.

Once the delivery system is placed in position, the rotation of the cylindrical rear part of the housing is stopped.

In this way, when the release mechanism is in a pressure-free state after the flaps with elastic members contract at the gripping point of the delivery mechanism on the bushing side, the delivery system coronary stent is held fixed, and when pressure is exerted on the pressure surface after contracting the pressure roller that exerts pressure on the protrusions on the gripping means flaps and causes the flaps with elastic members to open on the system gripping side, the delivery system coronary stent is released.

In the preparation for use, a coronary stent carried by the delivery system is first progressively inserted inside the device to which end the operator exerts pressure on the release means pressure surface, the release means flaps cause the pressure roller to contract, which in turn causes the protrusions arranged inside the roller on the gripping means flaps to contract and to open the flaps of the gripping means with elastic members at the gripping point of the delivery system on the bushing side so that the operator, through the hole in the cylindrical rear part of the housing, through the hole being formed between the gripping means flaps and also through the hole in the truncated front part of the housing, places the coronary stent delivery system inside the housing of the device. When no pressure is exerted on the outer pressure surface of the release means, the flaps no longer exert pressure on the pressure roller, the protrusions on the flaps within the pressure roller unfold, the flaps of the gripping means with elastic members contract at the gripping point of the delivery system on the bushing side and hold the delivery system. The operator manually advances the coronary stent carried by the delivery system placed within the device to the affected area of the coronary artery. Then, pressure is again exerted on the outer pressure surface of the release mechanism, the pressure roller causes the protrusions on the flaps to contract, the flaps open at the gripping point of the delivery system on the bushing side, and the operator brings the device to a necessary distance for fixing the same with his/her left arm, releases the pressure surface, and rotates the cylindrical rear part of the housing with his/her right arm to convert the rotary motion of the rear part of the housing into longitudinal translational motion of the runner with the gripping means along the guides inside the housing to displace the delivery system to a necessary distance for positioning of the coronary stent.

When exerting pressure on the pressure surface of the release means, the operator may also return the mechanism fixing the coronary stent delivery system into its initial position by rotating the cylindrical rear part of the housing in the necessary direction so that further positioning of the coronary stent forwards or backwards in each of the directions may be continued.

In an embodiment, the device may be already provided with the delivery system fixed therein. In this case, the stage of inserting in advance the coronary stent carried by the delivery system inside the device is omitted. The coronary stent carried by the delivery system is manually advanced to the affected area of the coronary artery and then pressure is exerted on the pressure surface, the flaps unfold at the gripping point of the delivery system, and the operator brings the device to a necessary distance for fixing the same with his/her left arm, releases the pressure surface, and rotates the cylindrical rear part of the housing with his/her right arm to displace progressively the delivery system to a necessary distance for positioning the coronary stent within the artery. When pressure is exerted on the pressure surface, by fixing the delivery system, the operator may also return to initial position the mechanism fixing the coronary stent delivery system by rotating the cylindrical portion of the housing in the necessary direction so that further positioning of the coronary stent forwards and backwards may be continued within the dimensions of the guides inside the housing in each of the directions.

In an embodiment, for a safe placing of the stent on the delivery system, a hollow tube prearranged inside the device may be used for inserting therein the delivery system carrying the stent following which the tube is removed from the device.

Listed below are the attached drawings wherein:

FIG. 1 is a general view of the device showing:
- 1—device housing,
- 2—truncated front part of the housing,
- 3—hole in the truncated front part of the housing for the delivery system,
- 4—recess for left arm fingers,
- 6—cylindrical portion of the front part of the housing,
- 7—slot for connection of the front part and cylindrical rear part of the housing,
- 8—cylindrical rear part of the housing,
- 21—release means pressure surface;

FIG. 2 is a top view showing:
- 1—device housing,
- 2—truncated front part of the housing,
- 4—recess for left arm fingers,
- 6—cylindrical portion of the front part of the housing,
- 8—cylindrical rear part of the housing,
- 21—release means pressure surface;

FIG. 3 is a side view showing:
- 1—device housing,
- 2—truncated front part of the housing,
- 4—recess for left arm fingers,
- 6—cylindrical portion of the front part of the housing,
- 7—slot for connection of the front part and rear part,
- 8—cylindrical rear part of the housing,
- 21—release means pressure surface;

FIG. 4 is a cross-sectional side view showing:
- 1—device housing,
- 3—hole in the truncated front part of the housing for the delivery system,
- 5—guides for displacement of the runner inside the housing,
- 6—cylindrical portion of the front part of the housing,
- 8—cylindrical rear part of the housing,
- 9—hole in the cylindrical rear part of the housing for the delivery system,
- 10—internal thread in the cylindrical rear part of the housing,
- 11—runner,
- 12—runner protrusion for connection to the thread of the cylindrical rear part of the housing,
- 14—runner guides,
- 15—gripping means,
- 17—hole in the gripping means for placing the delivery system,
- 18—pressure roller,
- 20—release means,
- 21—release means pressure surface,
- 22—release means flaps,
- 23—delivery system,
- 24—runner bushing,
- 26—gripping means flaps;

FIG. 5 is a general view of the delivery mechanism assembly with closed flaps, showing:
11—runner,
12—runner protrusion for connection to the internal thread of the cylindrical rear part of the housing,
13—position of joint between the gripping means bushing and the runner,
14—runner guides,
15—gripping means,
17—hole in the gripping means for placing the delivery system,
18—pressure roller,
20—release means,
21—release means pressure surface,
22—release means flaps,
24—runner bushing,
25—flaps protrusions,
26—gripping means flaps;

FIG. 5a is a general view of the delivery mechanism assembly with opened flaps, showing:
11—runner,
12—runner protrusion for connection to the internal thread of the cylindrical rear part of the housing,
13—position of joint between the gripping means bushing and the runner,
14—runner guides,
15—gripping means,
17—hole the in gripping means for placing the delivery system,
18—pressure roller,
20—release means,
21—release means pressure surface,
22—release means flaps,
25—flaps protrusions,
26—gripping means flaps.

FIG. 6 is a detached view of the device, showing:
11—runner,
12—runner protrusion for connection to the internal thread of the cylindrical rear part of the housing,
13—position of joint between the gripping means bushing and the runner,
14—runner guides,
15—gripping means,
16—flaps surface for rubber pads,
17—hole in the gripping means for placing the delivery system,
18—pressure roller,
19—elastic member,
20—release means,
21—release means pressure surface,
22—release means flaps,
25—flaps protrusions.

The invention will be described below with reference to the attached drawings.

Figure 1:
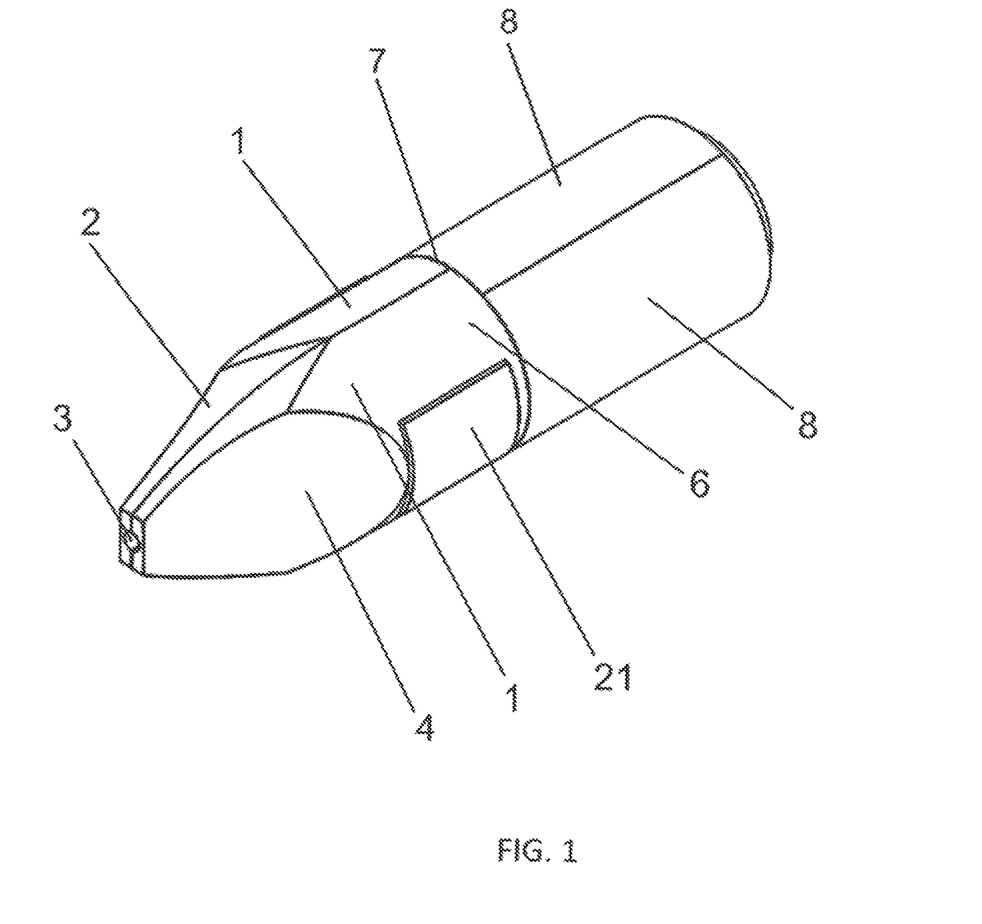
Figure 4:
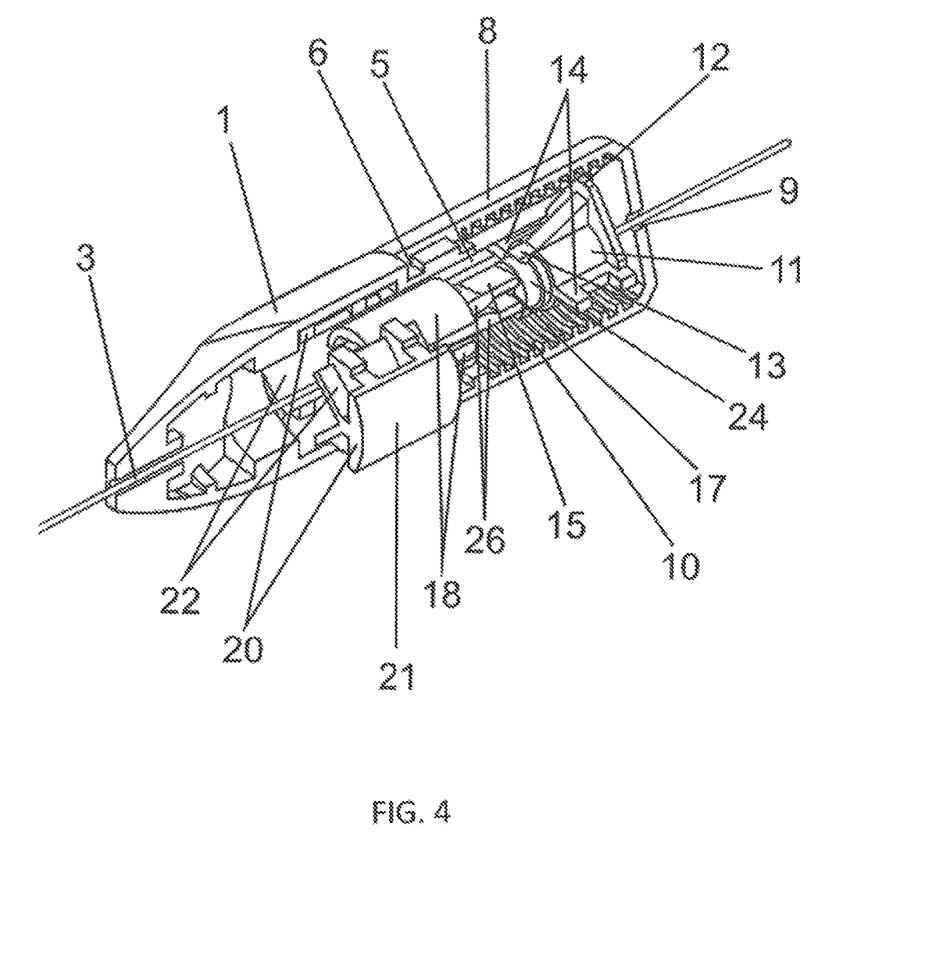
Figure 5:
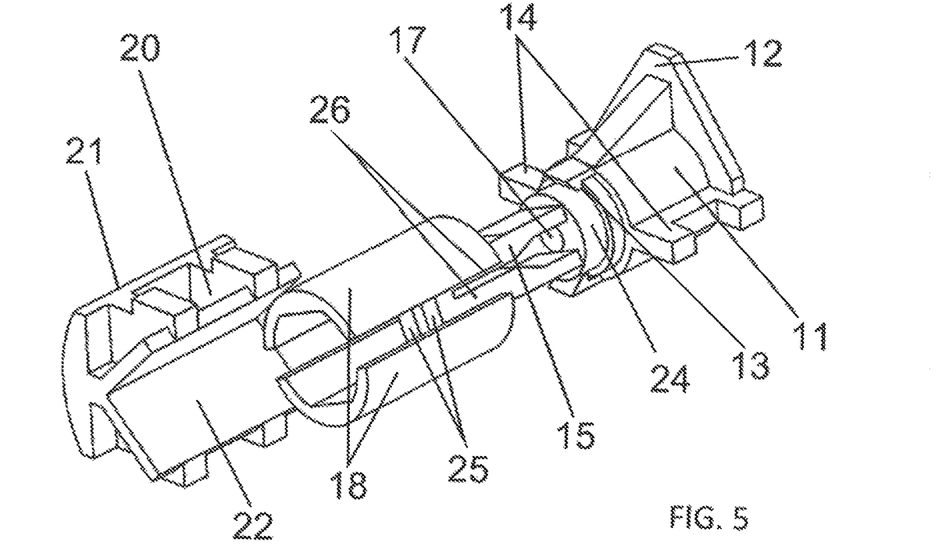
Figure 6:
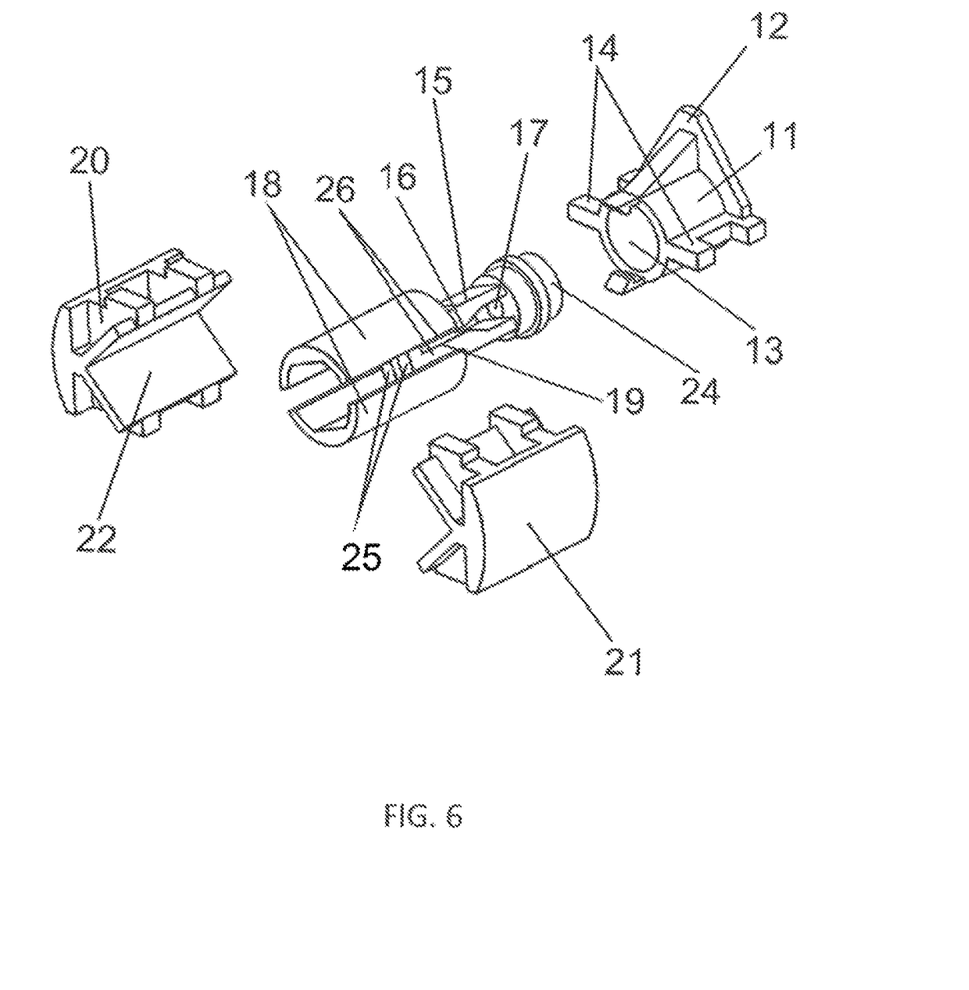

The device comprises a housing 1 (FIG. 1) formed of plastic by injection molding, wherein its surface is pebbled where it contacts the operator's 4 arm (FIG. 1), and the housing left and right halves (FIG. 1) are manufactured separately and assembled after placing therein a runner 11 (FIG. 4, FIG. 5, FIG. 5a, FIG. 6) with protrusions 12 (FIG. 4, FIG. 5, FIG. 5a, FIG. 6) for connection to an internal thread 10 of the cylindrical rear part 8 (FIG. 4) of the housing 1 and guides 14 (FIG. 4, FIG. 5, FIG. 5a, FIG. 6) movable along guides 5 (FIG. 4) inside the housing 1 (FIG. 4) connected by a bushing 24 (FIG. 4, FIG. 5, FIG. 6) to a gripping means 15 (FIG. 4, FIG. 5, FIG. 5a, FIG. 6) with flaps 26 (FIG. 4) having elastic members 19 (FIG. 6) at the gripping point of the delivery mechanism is gripped that are arranged inside the bushing 24 (FIG. 4, FIG. 5, FIG. 6) freely rotatably around its axis and with protrusions 25 (FIG. 5, FIG. 6) on the other end arranged inside a pressure roller 18 (FIG. 4, FIG. 5, FIG. 5a, FIG. 6) comprising two halves and contacting flaps 22 (FIG. 4, FIG. 5, FIG. 5a, FIG. 6) of a release means 20 (FIG. 4, FIG. 5, FIG. 5a, FIG. 6) arranged at an angle to each other and to the pressure roller 18 and cooperating with a pressure surface 21 (FIG. 4, FIG. 5, FIG. 5a, FIG. 6) of the release means 20 (FIG. 4, FIG. 5, FIG. 5a, FIG. 6) on an outer side of the housing 1 (FIG. 1, FIG. 2, FIG. 3).

Figure 2:
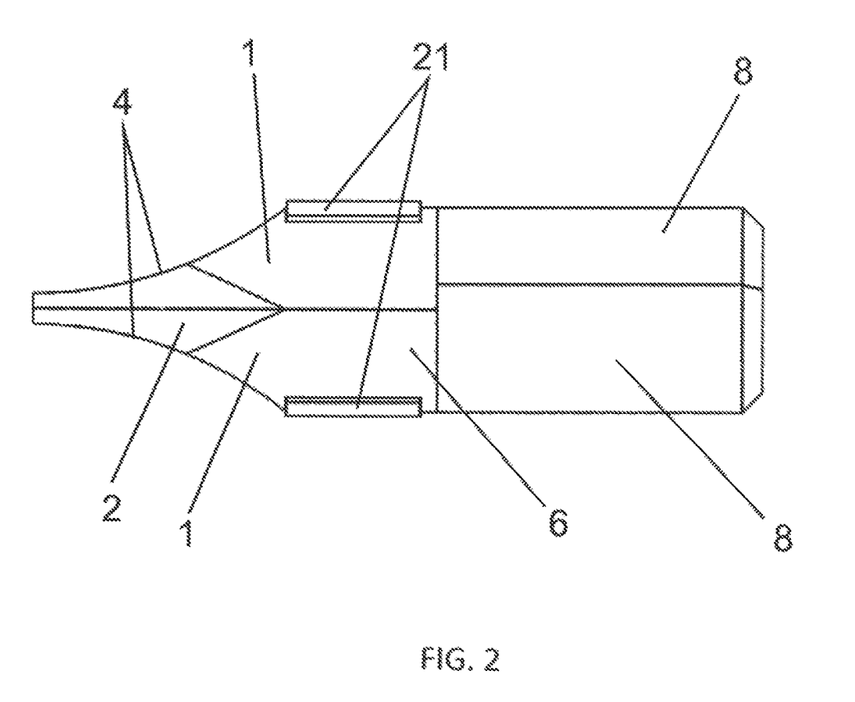
Figure 3:
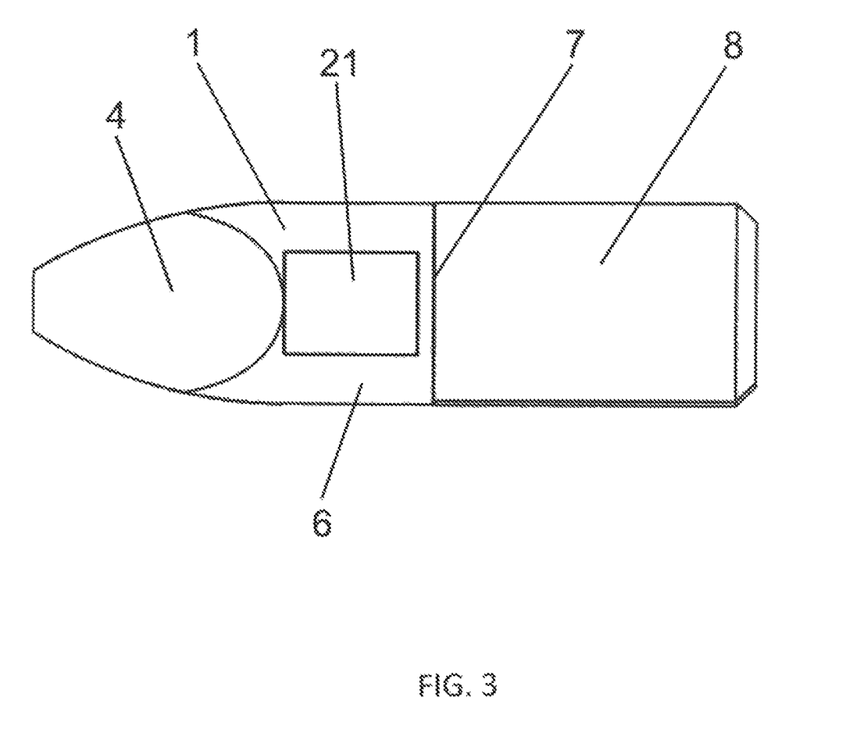

For placing a delivery system 23 (FIG. 4) inside the device, the operator exerts pressure with his/her right arm fingers on the pressure surface 21 (FIG. 4) of the release means 20 (FIG. 4) whose flaps 22 (FIG. 4) arranged inside the front part 2 of the housing 1 (FIG. 4) at an angle to each other and to the pressure roller 18 exert pressure on the surface of the pressure roller 18 comprising two halves (FIG. 4, FIG. 5, FIG. 5a, FIG. 6) which in turn cause the protrusions 25 (FIG. 5) on the flaps 26 (FIG. 5) of the gripping means 15 (FIG. 4, FIG. 5, FIG. 5a, FIG. 6) to contract as a result of which the ends of flaps 26 (FIG. 4, FIG. 5) of the gripping means 15 (FIG. 4, FIG. 5, FIG. 5a, FIG. 6) with elastic members 19 open at the point of gripping the delivery system 23 (FIG. 5a) to set free a through hole 17 in the gripping means 15 (FIG. 6) for insertion of the delivery system 23 (FIG. 4) into the device housing 1. The delivery system 23 (FIG. 4) is inserted into the device through holes 3, 9 (FIG. 4) in the front and rear parts of the housing 1 (FIG. 4) and the hole 17 between the flaps 26 (FIG. 4, FIG. 5a) of the gripping means 11 (FIG. 4, FIG. 5a) following which the operator releases the pressure surface 21 (FIG. 1, FIG. 2, FIG. 4), the pressure roller 18 causes the protrusions 25 (FIG. 5a) on the flaps 26 (FIG. 5a) of the gripping means 15 to contract, and the delivery system 23 (FIG. 4) is fixed between the flaps 26 (FIG. 5) with elastic members 19 (FIG. 4) of the gripping means 15 flaps (FIG. 4), and the operator rotates with his/her right arm fingers the cylindrical rear part 8 of the housing 1 around circumference 6 (FIG. 1, FIG. 3) in the necessary direction converting thereby the rotary motion of the rear part of the housing 8 into translational motion of the gripping means 15 and the runner 11 (FIG. 4), wherein the runner 11 (FIG. 4) protrusion 12 (FIG. 4) in cooperation with the internal thread 10 (FIG. 4) of the cylindrical rear part 8 (FIG. 4) of the housing 1 displaces the runner 11 and the gripping means 15 (FIG. 4) with the delivery system 23 (FIG. 4) longitudinally along the guides 5 (FIG. 4) inside the housing 1 to a necessary distance.

In an embodiment of the invention, the delivery system may be removed from the device to which end the delivery system is returned to initial position by causing the cylindrical rear part of the housing to rotate backwards, exerting pressure on the release means pressure surface, using the pressure roller to cause the protrusions on the gripping means flaps to contract inside the pressure roller and the gripping means flaps with elastic members to unclamp so that the delivery system is released.

In an embodiment of the embodiment, a device may be used with the delivery system 23 (FIG. 4) fixed therein in advance and in this case it is unnecessary to preinstall the delivery system inside the device.

In another embodiment of the invention, for a safe placing of the stent on the delivery system, a hollow tube prearranged inside the device may be used for inserting therein the delivery system 23 (FIG. 5) carrying the stent following which the tube is removed from the device.

The invention claimed is:

1. A device for positioning of a stent within coronary arteries comprising a housing with a through hole for placing a coronary stent delivery system, said housing comprising a truncated front part with recesses for the operator's arm and a pressure surface on an outer lateral surface of the housing, and a cylindrical rear part connected to the front part rotatably relative to the front part and provided with a circumferential thread in contact with a protrusion on a runner arranged inside the cylindrical rear part so as to be displaceable along guides inside the housing and by means of a bushing connected to a gripping means provided with flaps with elastic members at a gripping point of the delivery system on a bushing side and with protrusions provided on an opposite side and arranged within a pressure roller comprising two halves and contacting a release means inner surface arranged inside the housing and comprising flaps in the forms of plates arranged at an angle to each other and to the pressure roller and fixedly connected to the release means having the pressure surface in the form of plates on the outer lateral surface of the truncated front part of the housing.

2. The device according to claim 1, wherein the runner further comprises a number of protrusions contacting the circumferential thread inside of the cylindrical rear part of the housing.

3. The device according to claim 1, wherein the housing is formed of plastic, wherein a surface contacting the operator's arm is pebbled.

4. The device according to claim 1, wherein the device is provided with a delivery system fixed therein in advance and carrying a stent.

5. The device according to claim 1, wherein a hollow tube is inserted therein in advance for placing a delivery system carrying a stent.

6. A method for positioning of a coronary stent within coronary arteries comprising:
placing a coronary stent delivery system within a device housing by means of;
exerting pressure on a release means pressure surface arranged on an outer truncated part of the housing, wherein an inner part of the release means is arranged within the housing and comprises flaps in the form of plates arranged at an angle to each other and to a pressure roller and is fixedly connected to the release means, wherein the flaps cooperate with the pressure roller causing protrusions arranged within the pressure roller on gripping means flaps to contract, and causing flaps with elastic members to open, wherein the flaps with elastic members are arranged rotatably around their axis in a bushing provided inside a cylindrical rear part of the housing and is connected to a runner arranged in the rear part of the housing to form a hole, wherein the delivery system is placed inside the housing through openings in a front part and the rear part of the housing,
releasing the pressure surface such that the coronary stent delivery system is fixed inside the device housing, following which the delivery system, by means of rotation of the cylindrical rear part of the housing circumferentially relative to the front part of the housing, is displaced longitudinally along runner guides inside the housing to a necessary distance, wherein the rotary motion of the cylindrical rear part of the housing is converted into translational motion of the gripping means and the runner as a result of engagement of a protrusion arranged on the runner guides with a thread on an inner surface of the cylindrical rear part of the housing, wherein to return the delivery system to an initial position, the cylindrical rear part of the housing is caused to rotate backwards, and pressure is exerted on the release means pressure surface, and the protrusions on the gripping means flaps are caused to contract inside the pressure roller so that the gripping means flaps with elastic members unclamp and the delivery system is released.

\* \* \* \* \*